US009339280B2

(12) United States Patent
Collazo et al.

(10) Patent No.: US 9,339,280 B2
(45) Date of Patent: May 17, 2016

(54) SPOT FACING TROCHLEAR GROOVE

(71) Applicant: Stryker Corporation, Kalamazoo, MI (US)

(72) Inventors: Carlos E. Collazo, Old Greenwich, CT (US); Damon J. Servidio, Towaco, NJ (US); Arnold Douglas Scheller, Milton, MA (US)

(73) Assignee: Stryker Corporation, Kalamazoo, MI (US)

( * ) Notice: Subject to any disclaimer, the term of this patent is extended or adjusted under 35 U.S.C. 154(b) by 379 days.

(21) Appl. No.: 13/933,672

(22) Filed: Jul. 2, 2013

(65) Prior Publication Data
US 2013/0296869 A1    Nov. 7, 2013

Related U.S. Application Data

(63) Continuation of application No. 12/380,589, filed on Feb. 27, 2009, now Pat. No. 8,480,753.

(51) Int. Cl.
*A61B 17/17* (2006.01)
*A61B 17/88* (2006.01)
(Continued)

(52) U.S. Cl.
CPC ......... *A61B 17/1764* (2013.01); *A61B 17/1739* (2013.01); *A61F 2/3877* (2013.01); *A61B 2017/320052* (2013.01); *A61B 2017/90* (2013.01)

(58) Field of Classification Search
CPC ........... A61B 17/1739; A61B 17/1764; A61B 2017/320052; A61B 2017/90; A61F 2/3877
See application file for complete search history.

(56) References Cited

U.S. PATENT DOCUMENTS 5,035,699 A    7/1991    Coates
5,314,482 A    5/1994    Goodfellow et al.
(Continued)

FOREIGN PATENT DOCUMENTS

FR    2740325 A1    4/1997
WO    9104715 A1    4/1991
(Continued)

OTHER PUBLICATIONS

International Search Report and Written Opinion, PCT/US 10/00608, dated Jun. 29, 2010.
(Continued)

*Primary Examiner* — Larry E Waggle, Jr.
(74) *Attorney, Agent, or Firm* — Lerner, David, Littenberg, Krumholz & Mentlik, LLP

(57) ABSTRACT

The present invention relates to systems and methods for preparing the trochlear groove of a patient's femur to receive a prosthesis thereon. In the system, a combination drill-and-alignment guide includes at least a proximal and intermediate section, and preferably also includes a distal section. Guide holes for receiving guide pins therein are located in the proximal and distal sections of the guide. After the guide is positioned using at least one of several visual and/or tactile guide references in the system, the guides pins are placed through the guide holes of the guide and into bone. The guide may then be removed and replaced by cannulated reamers that are rotated and used to resect a predetermined amount of bone around the guide pins. A prosthesis having at least a portion of an outer surface that substantially matches the trochlear groove of the patient in a pre-degenerated state is then implanted on the resected bone.

20 Claims, 12 Drawing Sheets

(51) Int. Cl.
*A61F 2/38* (2006.01)
*A61B 17/90* (2006.01)
*A61B 17/32* (2006.01)

(56) References Cited

U.S. PATENT DOCUMENTS

| | | | |
|---|---|---|---|
| 5,403,322 | A | 4/1995 | Herzenberg et al. |
| 5,415,662 | A | 5/1995 | Ferrante et al. |
| 5,554,158 | A | 9/1996 | Vinciguerra et al. |
| 5,571,196 | A | 11/1996 | Stein |
| 5,601,565 | A | 2/1997 | Huebner |
| 5,702,459 | A | 12/1997 | Hummer et al. |
| 5,702,467 | A | 12/1997 | Gabriel et al. |
| 5,824,098 | A | 10/1998 | Stein |
| 6,171,340 | B1* | 1/2001 | McDowell ........... A61F 2/30724 623/18.11 |
| 6,254,605 | B1 | 7/2001 | Howell |
| 6,520,964 | B2 | 2/2003 | Tallarida et al. |
| 6,610,067 | B2 | 8/2003 | Tallarida et al. |
| 6,616,696 | B1 | 9/2003 | Merchant |
| 6,679,917 | B2 | 1/2004 | Ek |
| 6,712,856 | B1 | 3/2004 | Carignan et al. |
| 6,800,094 | B2 | 10/2004 | Burkinshaw |
| 6,905,514 | B2 | 6/2005 | Carignan et al. |
| 7,896,883 | B2 | 3/2011 | Ek et al. |
| 2003/0033018 | A1 | 2/2003 | Merchant |
| 2003/0120346 | A1 | 6/2003 | Mercinek et al. |
| 2003/0181984 | A1 | 9/2003 | Abendschein |
| 2003/0236521 | A1* | 12/2003 | Brown ............... A61B 17/1615 606/80 |
| 2004/0153087 | A1 | 8/2004 | Sanford et al. |
| 2005/0119664 | A1 | 6/2005 | Carignan et al. |
| 2005/0143830 | A1 | 6/2005 | Marcinek et al. |
| 2005/0143833 | A1 | 6/2005 | Merchant |
| 2005/0171612 | A1 | 8/2005 | Rolston |
| 2005/0177242 | A1 | 8/2005 | Lotke |
| 2005/0267584 | A1 | 12/2005 | Burdulis et al. |
| 2006/0009776 | A1 | 1/2006 | Justin et al. |
| 2006/0009855 | A1 | 1/2006 | Goble et al. |
| 2006/0241634 | A1 | 10/2006 | Tuttle et al. |
| 2006/0276796 | A1 | 12/2006 | Creger et al. |
| 2007/0100459 | A1 | 5/2007 | Rhodes |
| 2007/0198022 | A1 | 8/2007 | Lang et al. |
| 2007/0219639 | A1 | 9/2007 | Otto et al. |
| 2007/0270711 | A1 | 11/2007 | Gil et al. |
| 2007/0288021 | A1* | 12/2007 | Rickels ............... A61B 17/1764 606/916 |
| 2007/0299528 | A9 | 12/2007 | Lotke |
| 2008/0172125 | A1 | 7/2008 | Ek |
| 2008/0195221 | A1 | 8/2008 | Howald et al. |
| 2008/0300689 | A1 | 12/2008 | McKinnon et al. |
| 2012/0259335 | A1 | 10/2012 | Scifert et al. |

FOREIGN PATENT DOCUMENTS

| | | |
|---|---|---|
| WO | 0013616 A1 | 3/2000 |
| WO | 03013339 A2 | 2/2003 |
| WO | 2005069809 A2 | 8/2005 |
| WO | 2006127486 | 11/2006 |
| WO | 2010123836 A1 | 10/2010 |

OTHER PUBLICATIONS

Zimmer Gender Solutions, Increased Trochlear Groove Angle, website printout, 2 pages, Aug. 2008.

Extended European Search Report for Application No. EP 10746569 dated Jun. 27, 2014.

* cited by examiner

SPOT FACING TROCHLEAR GROOVE

CROSS REFERENCE TO RELATED APPLICATIONS

This application is a continuation of U.S. application Ser. No. 12/380,589, filed on Feb. 27, 2009, the entire disclosure of which is incorporated herein by reference.

FIELD OF THE TECHNOLOGY

The present invention relates to an apparatus and method for preparing the trochlear groove of a patient's femur to receive a prosthesis thereon, and in particular, relates to positioning a guide on the patient's femur that aides in the resection of the femur such that the prosthesis may be implanted on the resected bone.

BACKGROUND OF THE INVENTION

Patello-femoral joint disease is a condition in which the articular cartilage of the patella and/or the femoral trochlear groove is eroded due to osteoarthritis resulting in some cases in severe anterior knee pain. For patients with isolated patello-femoral joint disease who otherwise show no evidence of the disease present in the tibiofemoral joint, or for patients with a history of chronic patella dislocations, a patello-femoral joint replacement offers a beneficial alternative to total joint replacement. Moreover, a patello-femoral joint replacement provides pain relief or improved patella tracking while preserving significantly more bone than a total joint replacement.

In total joint replacement, portions of a patient's trochlear groove, medial and lateral condyles, and tibial plateau are generally resected. In patello-femoral joint replacement, generally only the patella and the trochlear groove are replaced. Bone preservation is an important consideration in opting for patello-femoral joint replacement for the patient. Other benefits of patello-femoral joint replacement in view of total joint replacement may include less cost as well as less rehabilitation time for the patient.

Current patello-femoral joint replacement systems employ different types of instruments that remove bone in the trochlear groove region of the femur. For instance, bone adjacent the intercondylar notch of the trochlear groove may be removed with an osteotome, rasp, reciprocating or oscillating saw, or burr, or more likely, with a combination of these known resection instruments in the art. However, there is very little control of the shape and depth of the resection made by these tools. Perhaps the biggest drawback of the instruments mentioned above is that each provides no true anatomically based means of restoring the trochlear groove or patella track to ensure proper patello-femoral kinematics. There is no systematic approach to ensure that the bone being resected will be replaced with a prosthesis that will be implanted on the resected bone.

During a procedure to restore the patella track of a patient in a patello-femoral joint replacement, it is important to ensure that the prosthesis that will be implanted does not restrict flexion of the knee by raising the patella anteriorly and/or effect the natural track of the patella by not accurately restoring the "Q angle" of the trochlear groove defined by the lines representing the pull of the quadriceps muscle and the axis of the patellar tendon.

SUMMARY OF THE INVENTION

A first aspect of the present invention is an apparatus for preparing the trochlear groove of a patient's femur to receive a prosthesis thereon. According to this aspect, the apparatus is an elongate guide utilized for inserting a plurality of guide pins therethrough along the trochlear groove of a patient's femur. The guide includes a proximal section preferably oriented along what may be referred to as the generally curved portion of the trochlear groove which tracks the pull of the quadriceps tendon. This curved portion may be referred to as the sagittal curve of the trochlear groove. The proximal section preferably has a first guide hole configured to receive a first guide pin therethrough.

The guide preferably further includes an intermediate section extending distally from the proximal section. The intermediate section has at least one guide hole configured to receive a guide pin therethrough. Preferably, the intermediate section has a second guide hole configured to receive a second guide pin therethrough and a third guide hole configured to receive a third guide pin therethrough. The first guide hole of the proximal section is preferably located laterally of the at least one guide hole of the intermediate section.

In an embodiment of this first aspect of the present invention, the guide is part of a system used to accurately restore the trochlear groove of a patient's femur with the aid of at least one reference member. A first reference member may be a flexible sizing membrane attached to a bone contacting surface of the guide. The flexible sizing membrane is a generally thin and pliable member having a perimeter that substantially matches or is rather identical to the perimeter of a prosthesis that will be implanted on the resected bone of the femur. Preferably, the bone contacting surface of the guide tracks the trochlear groove of the patient's femur. The combination of the bone contacting surface of the guide and flexible sizing membrane preferably act as visual and tactile references for locating an optimal position of the guide before any bone resection occurs.

A second aspect of the present invention is a method of preparing the trochlear groove to receive a prosthesis thereon. The method preferably includes placing an elongate guide along a portion of a trochlear groove of the femur. The guide preferably has a proximal section and an intermediate section extending distally from the proximal section, wherein the proximal section includes a first guide hole therethrough and the intermediate section includes a second and third guide hole therethrough. The first guide hole is preferably located laterally of the second guide hole and the third guide hole. The method preferably further includes inserting respective first, second and third guide pins through the first, second and third guide holes until the guide pins are secured to bone of the femur. The method preferably further includes removing the guide from the first, second and third guide pins and placing respective first, second and third bone cutting instruments on the first, second and third guide pins in order to form three overlapping recessed areas in the trochlear groove of the patient's femur. The three overlapping recessed areas preferably conform to three overlapping areas of a prosthesis that will be implanted on the resected bone.

In one embodiment according to the second aspect of the present invention, the first, second and third bone cutting instruments preferably do not all resect bone along parallel axes. Preferably, the first cutting instrument resects bone along a longitudinal axis that is not parallel to a longitudinal axis that the second cutting instrument resects bone along. Preferably, the second cutting instrument resects bone along a longitudinal axis that is parallel to a longitudinal axis that the third cutting instrument resects bone along. The orientation of the longitudinal axes of the first, second and third cutting instruments determines the angle or angles between first, second and third sections of the prosthesis that will be implanted on the resected bone.

According to this second aspect, the method preferably includes removing the guide from the trochlear groove of the femur such that the elongate guide does not surround any of the first, second, or third guide pins each secured to bone. The method preferably further includes placing first, second and third bone cutting instruments or bone cutting instruments or reamers each having a guide hole therein against a first, second and third bone surface of the trochlear groove respectively, such that the first, second and third guide pins are located in the guide holes of the first, second and third bone cutting instruments respectively. The method preferably further includes, rotating the first, second, and third bone cutting instruments to form a first, second and third recess in the bone of the femur.

A third aspect of the present invention is a prosthesis for implantation in a prepared trochlear groove of a femur. According to this aspect, the prosthesis comprises a proximal section having a first maximum height in an anterior-posterior direction and a first diameter, an intermediate section having a second maximum height in an anterior-posterior direction and a second diameter, and a distal section having a third maximum height in an anterior-posterior direction and a third diameter. Preferably, the second maximum height is less than the first maximum height, and the third maximum height is less than the second maximum height.

In one embodiment according to this third aspect, the proximal section, the intermediate section, and the distal section of the prosthesis each have an outer surface with a continuous groove configured to engage an articular surface of a patella. Preferably, the proximal section, the intermediate section, and the distal section each have a generally flat bone contacting surface. Preferably, the proximal, intermediate, and distal sections each have a side surface between the outer surface and bone contacting surface thereof, the side surfaces forming the first, second, and third diameters of the proximal, intermediate, and distal sections respectively.

Preferably, the first diameter of the prosthesis according to this aspect is greater than the second diameter. Preferably, the second diameter is greater than the third diameter. Preferably, the flat bone contacting surfaces of the intermediate section and the distal section lie along a same plane. Preferably, the flat bone contacting surface of the proximal section lies along a plane oriented at an angle with respect to the plane of the intermediate and distal sections.

Preferably, a portion of the first diameter of the proximal section intersects with a portion of the second diameter of the intermediate section, and the portion of the second diameter of the intermediate section intersects with a portion of the third diameter of the distal section.

A fourth aspect of the present invention is a system of preparing the trochlear groove of a femur to receive a prosthesis thereon. According to this aspect, the system includes an elongate guide having a proximal section adapted to engage the trochlear groove, the proximal section having a first guide hole therethrough, and an intermediate section extending distally from the proximal section, the intermediate section having a second guide hole therethrough and a third guide hole therethrough, wherein the first guide hole is located laterally of the second guide hole and the third guide hole. Preferably, the system further includes first, second and third guide pins each configured to engage bone along the trochlear groove of the femur along axes collinear with longitudinal axes of the first, second, and third guide holes respectively. Preferably, the system further includes first, second and third cutting instruments each configured to form a recess in bone along the trochlear groove of the femur along axes collinear with the longitudinal axes of the first, second and third guide pins respectively.

According to an embodiment of the fourth aspect, the prosthesis of the system further comprises a proximal section having a first maximum height in an anterior-posterior direction and a first diameter, an intermediate section having a second maximum height in an anterior-posterior direction and a second diameter, the second maximum height less than the first maximum height, and a distal section having a third maximum height in an anterior-posterior direction and a third diameter, the third maximum height less than the second height. The system may further comprise a flexible member having a shape approximating a surface area of the bone contacting surfaces of each of the proximal, intermediate, and distal sections of the prosthesis. Preferably, the proximal section, the intermediate section, and the distal section of the prosthesis each have a generally flat bone contacting surface. Preferably, the second diameter of the prosthesis is less than the first diameter, and the third diameter is less than the second diameter.

A fifth aspect of the present invention is a prosthesis for implantation in a prepared trochlear groove of a femur. According to this aspect, the prosthesis comprises a first section having a first maximum height in an anterior-posterior direction and a first diameter, and a second section having a second maximum height in an anterior-posterior direction and a second diameter, wherein the second maximum height is less than the first maximum height. Preferably, the first and second sections of the prosthesis each have an outer surface with a continuous groove configured to engage an articular surface of a patella. Preferably, the first and second sections each have a generally flat bone contacting surface. Preferably, first and second sections each have a side surface between the outer surface and bone contacting surface thereof, the side surfaces forming the first and second diameters of the first and second sections respectively. Preferably, the flat bone contacting surface of the first section lies along a plane oriented at an angle with respect to the plane of the second section. Preferably, the first diameter of the prosthesis according to this aspect is greater than the second diameter.

BRIEF DESCRIPTION OF THE DRAWINGS

The present invention will be better understood on reading the following detailed description of non-limiting embodiments thereof, and on examining the accompanying drawings, in which.

DETAILED DESCRIPTION

Figure 1:
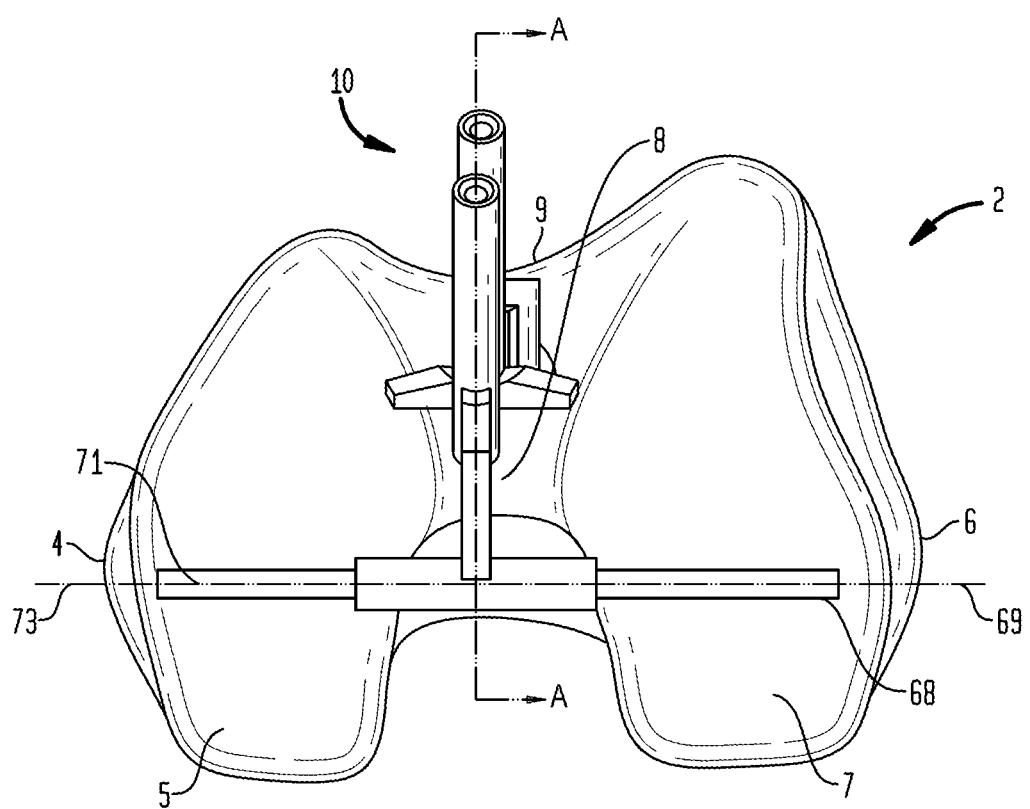
FIG. 1 is a view of a patient's distal femur showing an embodiment of a guide of the present invention generally positioned thereon.
Figure 2:
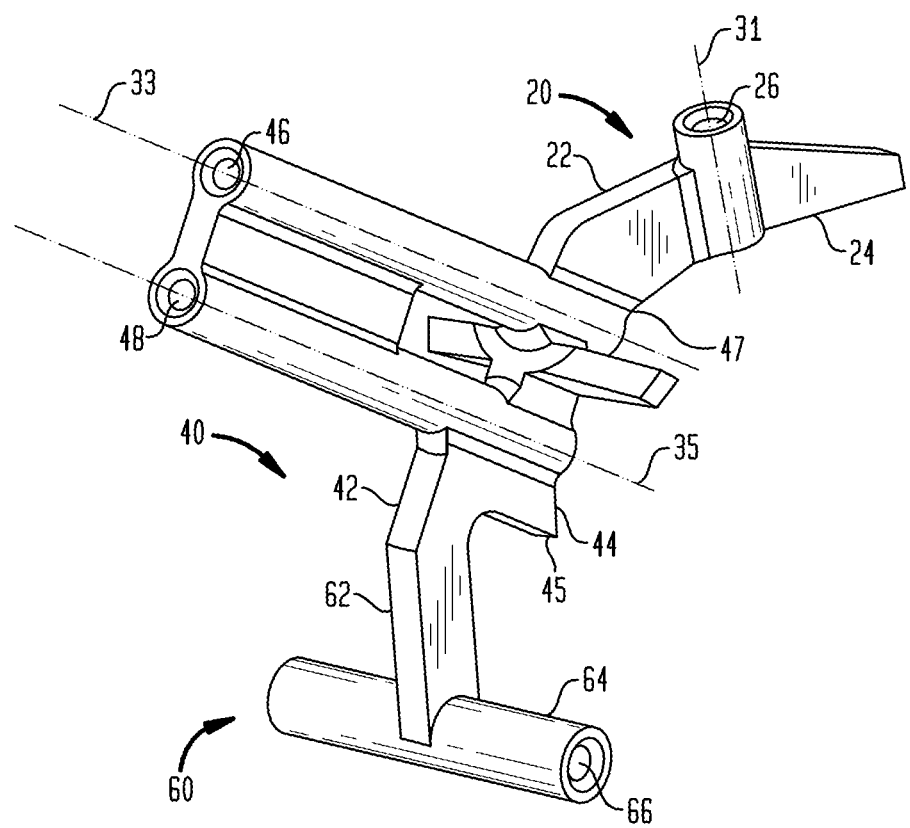
FIG. 2 is a perspective view of the guide of FIG. 1.

As used herein, when referring to bones or other parts of the body, the term "proximal" means closer to the heart and the term "distal" means more distant from the heart. The term "inferior" means toward the feet and the term "superior" means towards the head. The term "anterior" means towards the front part of the body or the face and the term "posterior" means towards the back of the body. The term "medial" means toward the midline of the body and the term "lateral" means away from the midline of the body.

The systems and methods that are described herein generally include the use of a family of multiple sized trochlear prostheses, a combination drill-and-alignment guide corresponding to each prosthesis, a flexible sizing membrane corresponding to each prosthesis, a series of guide pins to insert in guide holes of the combination drill-and-alignment guide, and a series of bone cutting instruments or reamers corresponding to specific sections of each prosthesis.

Referring to the drawings, wherein like reference numerals represent like elements, there is shown in the figures, in accordance with embodiments of the present invention, a combination drill-and-alignment guide or guide for preparing the trochlear groove of a patient's femur for resection, designated generally by reference numeral 10. As shown in FIGS. 1-5, guide 10 is designed to be used in preparing a damaged trochlear groove of a patient's femur for resection such that a prosthesis having an outer surface approximating the trochlear groove of the patient in a pre-degenerated state may be implanted on the resected bone and the trochlear groove of the patient may therefore be restored.

As shown in FIGS. 1-5, guide 10 is an elongate guide having a plurality of guide holes 26,46,48 configured to receive a plurality of guide pins 70,72,74 therein. Guide 10 preferably includes a proximal section 20 adapted to engage a trochlear groove 8 of a femur 2 along a curve 9 of the trochlear groove. Curve 9 generally follows along a plane parallel to the sagittal plane. Preferably, this plane is along the deepest portion of groove 8.

Figure 4:
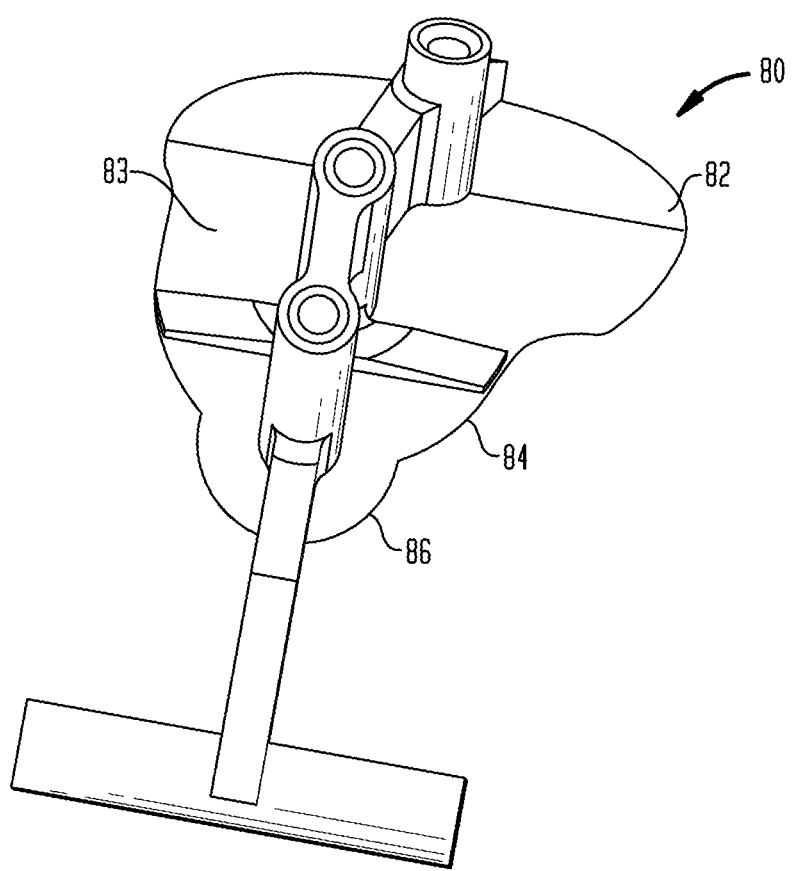
FIG. 4 is a perspective view of the guide of FIG. 1 positioned on an embodiment of a flexible sizing membrane.

Preferably, proximal section 20 has an outer surface 22 and a bone contacting surface 24. It should be understood that when guide 10 is used in combination with flexible sizing membrane 80 as shown in FIG. 4, bone contacting surface 24 of guide 10 contacts an outer surface 83 of flexible sizing membrane 80 rather than bone of femur 2. Preferably, bone contacting surface 24 of proximal section 20 of guide 10 has a shape that substantially follows along curve 9 of trochlear groove 8. Proximal section 20 preferably has a first guide hole 26 configured to receive a first guide pin 70 there through.

Guide 10 preferably includes an intermediate section 40 extending distally from proximal section 20. Intermediate section 40 has an outer surface 42 and a bone contacting surface 44. A distal portion 45 of bone contacting surface 44 preferably begins along trochlear groove 8 of the patient's femur 2 and follows trochlear groove 8 in a proximal direction. Bone contacting surface 44 preferably terminates just as curve 9 of trochlear groove 8 begins. Intermediate section 40 of guide 10 includes a second guide hole 46 configured to receive a second guide pin 72 therethrough and a third guide hole 48 configured to receive a third guide pin 74 therethrough. Preferably, first guide hole 26 is located laterally of second and third guide holes 46, 48.

Figure 3:
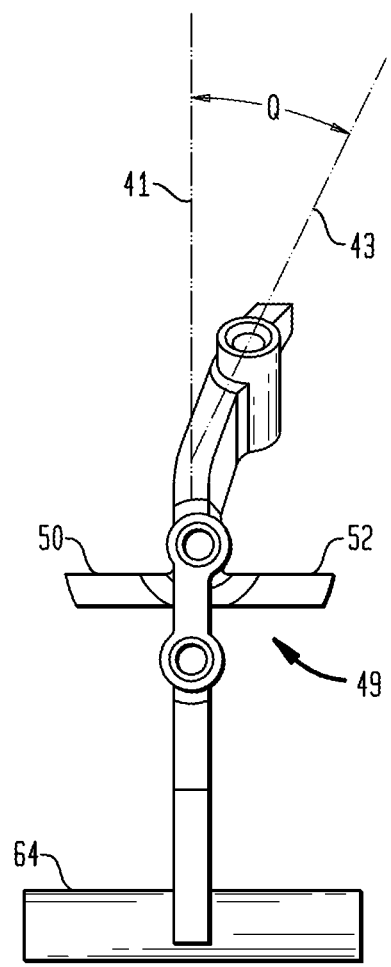
FIG. 3 is an anterior perspective view of the guide of FIG. 1 showing the angle between a proximal section and an intermediate section of the guide.

As shown in FIG. 3, intermediate section 40 preferably includes a first reference guide 49 extending in a medial-lateral direction from a longitudinal axis 41 of intermediate section 40. First reference guide 49 preferably includes a first wing 50 and a second wing 52. First reference guide 49 is preferably perpendicular to intermediate section 40 and acts as an aid in positioning guide 10 correctly along trochlear groove 8 of the patient's femur 2 such that the prosthesis that will be implanted on the resected bone will be implanted in a correct position. Preferably, first reference guide 49 of intermediate section 40 is adjacent an intercondylar region of femur 2 such that first and second wings 50,52 contact an intercondylar region of femur 2. First reference guide 49 is preferably configured to reference anatomic structures of femur 2 to aid in placement of guide 10.

Guide 10 may further include a distal section 60 extending distally from intermediate section 40. When guide 10 is positioned on trochlear groove 8 of femur 2, distal section 60 is preferably located between a medial condyle 5 and a lateral condyle 7 of the femur 2. Guide 10 preferably includes a second reference guide 64 extending in a medial-lateral direction from distal section 60. Second reference guide 64 is preferably perpendicular to distal section 60. Second reference guide preferably includes a hole 66 therethrough adapted to receive an elongate shaft 68 therein. Second reference guide 64 has a longitudinal axis 69 co-linear with a longitudinal axis 71 of elongate shaft 68.

Elongate shaft 68 is adapted to visually align second reference guide 64 to a transepicondylar axis 73 of femur 2. Transepicondylar axis 73 may be defined as a line that passes through a point on medial epicondyle 4 and lateral epicondyle 6. Second reference guide 64 is preferably configured to reference anatomic structures such as the medial epicondyle 4 and lateral epicondyle 6 of femur 2 to aid in placement of guide 10. The design of bone contacting surfaces 24, 44 of guide 10, the design of first and second reference guides 49, 64 and the design of flexible sizing membrane 80 all may act to correctly position guide 10 on trochlear groove 8 of femur 2.

As further shown in FIG. 3, each guide is made with a Q angle that matches that of a corresponding prosthesis. As generally known in the art, the Q angle is the angle formed by the lines representing the pull of the quadriceps muscle (generally axis 43) and the axis of the patellar tendon (generally axis 41). The choice of what sized guide should be used for a particular patient may be made from measurement data of the patient's femur from CT scans or other known methods in the art for obtaining the size of anatomical structures of a patient.

Figure 5:
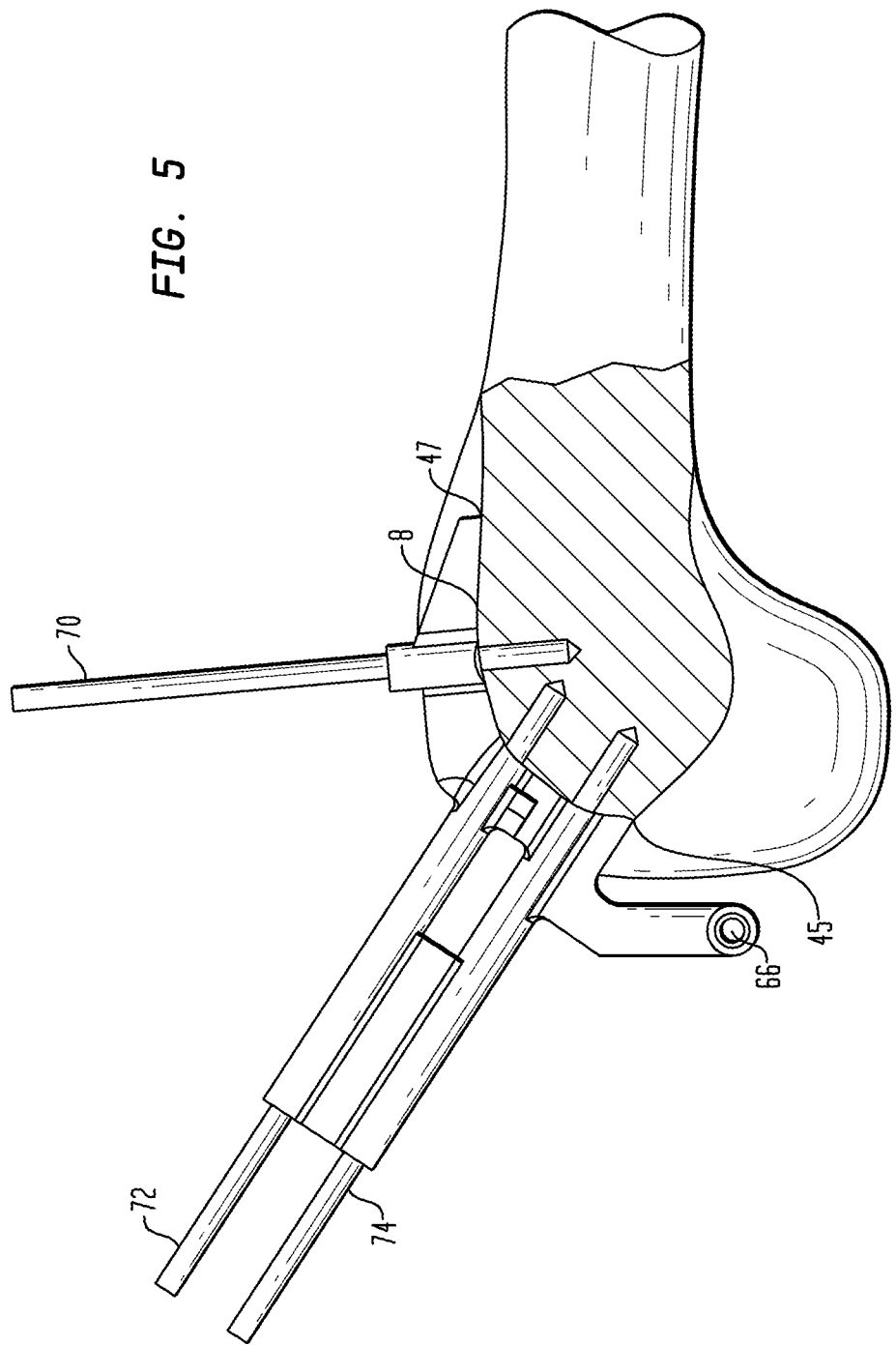
FIG. 5 is a partial cross-sectional lateral view of the patient's femur taken along line A-A of FIG. 1, showing the guide positioned along the trochlear groove of the femur.

In a method of the present invention, a guide 10 is selected that best suits a particular patient's anatomy. The patient's femur is then exposed and the bone contacting surface of the guide with or without the flexible sizing membrane attached thereto is placed along the damaged trochlear groove of the femur. Guide 10 may then be positioned along trochlear groove 8 without a flexible sizing membrane 80 as shown in FIG. 1 or rather attached to flexible sizing membrane 80 as shown in FIG. 4 (femur 2 not shown in FIG. 4). Guide 10 may be adjusted to ensure that it is resting adjacent to the lowest or deepest portion of the trochlear groove as shown in FIG. 5. Preferably, distal and proximal endpoints 45, 47 of the bone contacting surface of guide 10 rest tangent to the bone. At this time, positioning and alignment of guide 10 may be made by ensuring that first reference guide 49 is contacting adjacent bone in the intercondylar region of femur 2.

Placing guide 10 along the deepest part of trochlear groove 8 automatically sets guide 10 in about 3° to 5° degrees of external rotation, however, if another alignment check is desired, second reference guide 64 may be used. If so, elongate shaft 68 may be placed in hole 66 of second reference guide to visually align the second reference guide to transepicondylar axis 73 of the knee. It should be understood that in placing the guide along the deepest part of the trochlear groove anteriorly to the center of the intercondylar notch posteriorly, also known as Whiteside's Line, preferably results in guide 10 being perpendicular to transepicondylar axis 73 or approximately in about 3° to 5° of external rotation.

A further visual reference may be used with respect to the described systems and methods. As shown in FIG. 4, flexible sizing membrane 80 may be used as a visual reference of where the prosthesis that will be implanted on the resected bone will be located. Preferably, flexible sizing membrane 80 is positioned on the surface of the damaged femur before guide 10 is positioned. The perimeter of flexible sizing membrane 80 is preferably identical to that of prosthesis 120 and its flexibility ensures that it conforms to the irregular topography of the trochlear groove of the femur. The size of first, second and third sections 82,84,86 of flexible sizing membrane 80 preferably match that of first, second and third sections 124,126,128 of prosthesis 120 respectively. Flexible sizing membrane 80 is preferably made of a compliant material that naturally conforms to the shape of the bone in which it contacts. It preferably has a thin configuration such that bone contacting surface 24,44 of guide 10 may still effectively purchase bone of trochlear groove 8 as guide 10 is positioned on bone of femur 2.

After guide 10 is positioned on the exposed bone of the femur with or without flexible sizing membrane 80, first, second and third drill or guide pins 70,72,74 are then inserted into the bone through first, second and third guide holes 26, 46, 48 of guide 10 respectively as shown in FIG. 5. Pins 70,72,74 may be drill bits that are drilled into the bone of the femur or may rather be pins having threads that may threaded into the bone. It should be understood that pins 70,72,74 may be configured in any manner such that each may penetrate bone and be securely engaged to the bone.

In order for guide 10 to be removed from pins 70,72,74 such that reaming or resection of the bone may take place, one or more pins may have to be removed from the bone of the femur that each is secured into. For instance, to remove guide 10, first pin 70 may be removed such that guide 10 may be removed from pins 72,74 secured to bone. After guide 10 is removed, first pin 70 may then be secured back into position in bone.

Figure 7:
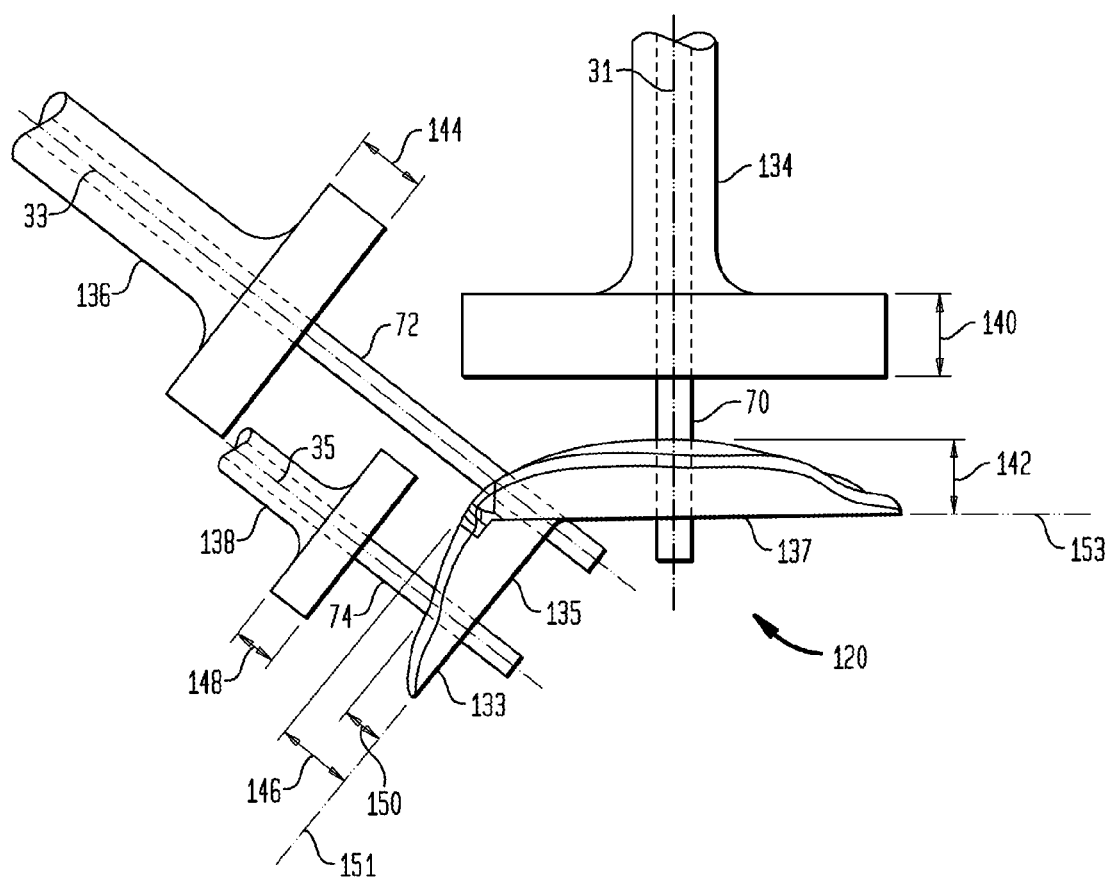
FIG. 7 is an elevation view of the prosthesis of FIG. 6 and three different sized reamers used in resecting bone of the patient's femur.
Figure 10:
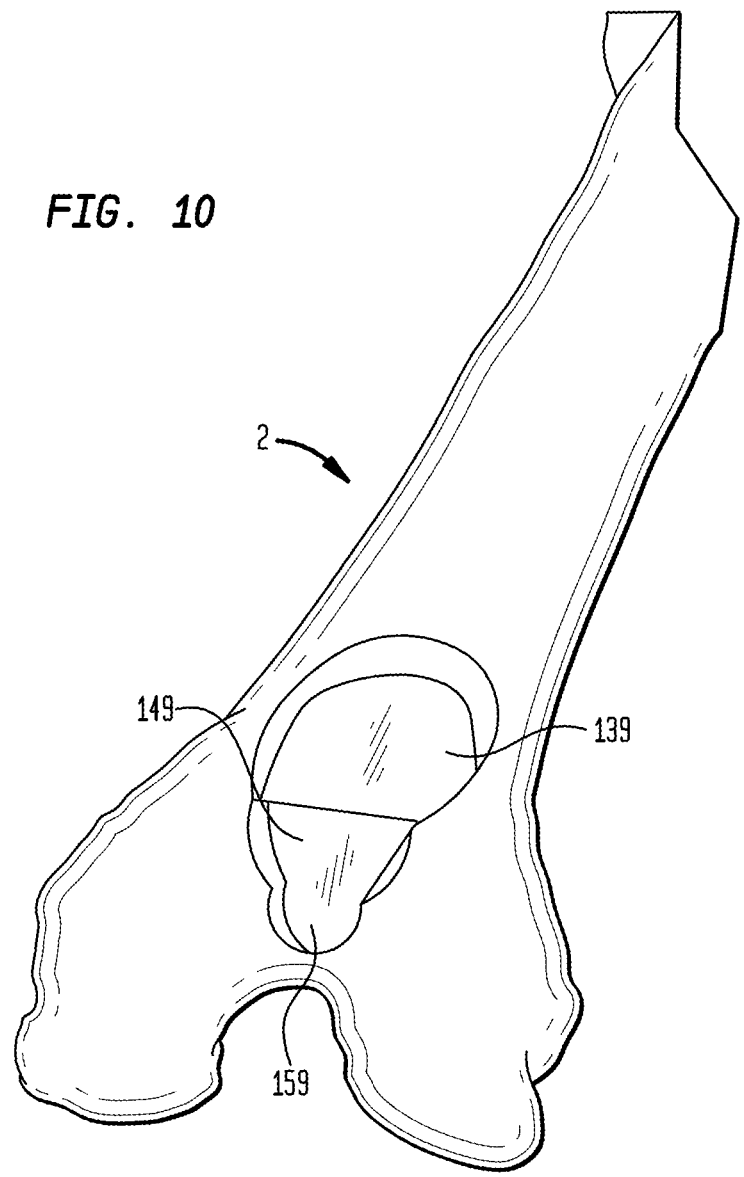
FIG. 10 is a perspective view of a patient's femur after the trochlear groove has been resected.

As shown in FIG. 7, first, second and third drill pins 70,72, 74 are used to guide first, second and third bone cutting instruments or cannulated spot-facing reamers 134,136,138 respectively. Also shown in this Figure is prosthesis 120 for representing the relationship among the reamers, pins, and respective sections of prosthesis 120 only. At this time in the method of the present invention, pins 70,72,74 are secured into bone and reaming or resection of the bone is ready to occur. In order for the resection of the bone to take place, one or more pins 70,72,74 may have to be removed from the bone of the femur that each is secured into. For instance, reamers 134 may only be able to rotate and resect bone if pin 72 is not secured into bone since part of the perimeter of second reamer 136 or pin 72 itself may overlap with the perimeter of reamer 134. Regardless of whether each pin 70,72,74 may be secured into bone when reamers 134,136,138 are resecting bone, the result of utilizing each reamer 134,136,138 is that three overlapping recesses are created in the bone of the femur along the trochlear groove as shown in FIG. 10.

As shown in FIG. 7, to control the depth of each cut, cutting instruments or reamers 134,136,138 are plunged into femur 2 to a depth approximately equaling its respective height 140, 144,148. The height 140,144,148 of each reamer is substantially equal to the maximum thickness 142,146,150 of first, second and third sections 124,126,128 of prosthesis 120 respectively. It should be understood that reamers 134,136, 138 may plunged into femur 2 to a depth less than respective heights 140,144,148 based on the corresponding height of first, second and third sections 124,126,128 of prosthesis 120.

Figure 9:
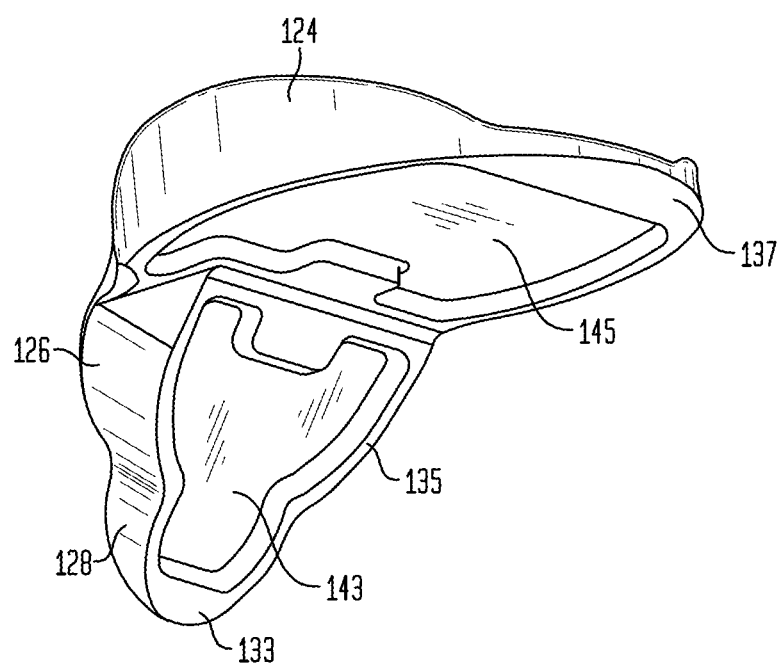
FIG. 9 is a perspective view of the bone contacting surface of the prosthesis of FIG. 6.

Second and third reamers 136,138 resect bone such that a plane 151 of resected bone is preferably created. First reamer 153 resects bone such that a plane 153 is created, wherein plane 153 is angled with respect to plane 151. Second and third bone contacting surfaces 133,135 of prosthesis 120 are configured to matingly engage plane 151. First bone contacting surface 137 of prosthesis 120 is configured to matingly engage plane 153. It should be understood that while bone contacting surfaces 133,135,137 of prosthesis 120 are shown as flat in FIGS. 7 and 9, other geometric configurations of surfaces 133,135,137 may be present without departing from the scope of the present invention. As shown in FIG. 9, recess 143 is located in bone contacting surfaces 133,135 and recess 145 is located in bone contacting surface 137. Recesses 143 and 145 may be formed in prosthesis 120 to house bone cement or any other like biocompatible material for joining prosthesis 120 to the resected bone of the patient's femur.

Figure 11:
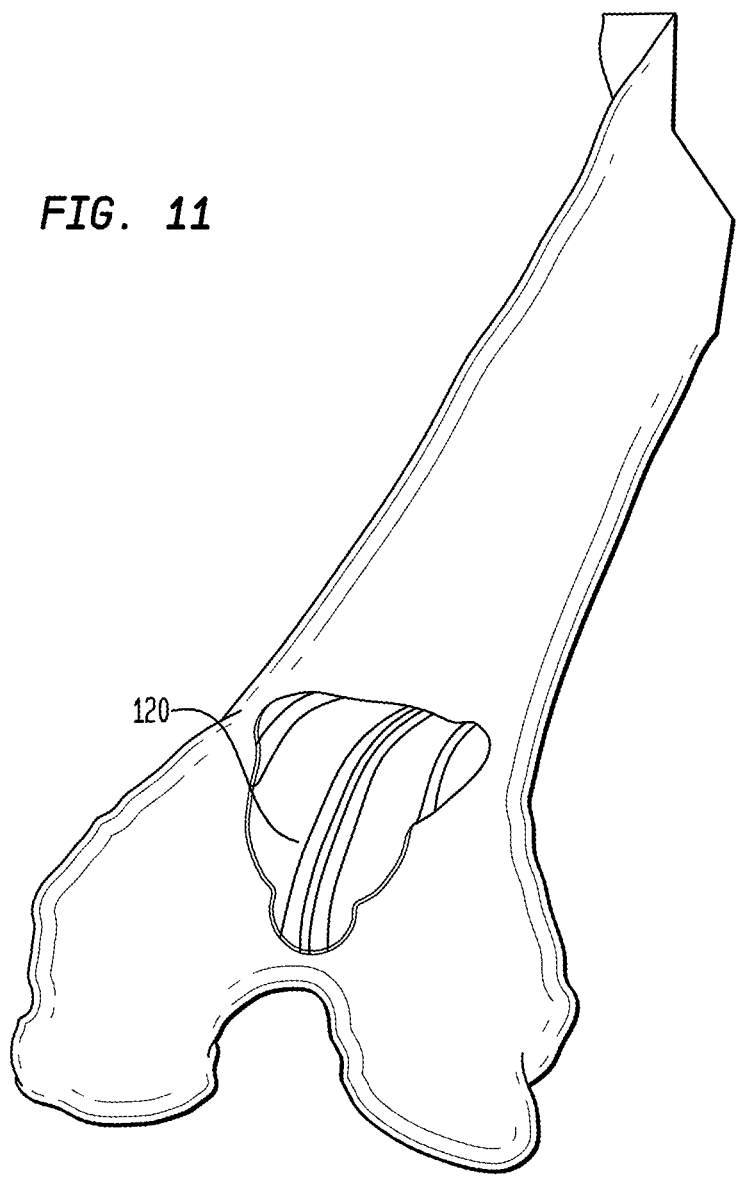
FIG. 11 is a perspective view of the femur shown in FIG. 10 having a prosthesis implanted on the resected bone of the trochlear groove.

Reamers 134,136,138 are used in order to create recessed cuts or counter bores in the patient's femur along the trochlear groove. The cuts made by reamers 134,136,138 are used in order to correctly seat prosthesis 120 on the resected bone. As shown in FIG. 10, first, second and third reamers 134,136,138 create first, second and third recesses 139,149,159 in the patient's femur respectively. After each recess or cut is completed, prosthesis 120 may then be placed in the prepared cavity and impacted until full seating is achieved as shown in FIG. 11. Prosthesis 120 may be cemented in place and may be made with a variety of bone ingrowth surfaces, such as beads, Ti-foam, HA coating or any other known biocompatible bone ingrowth material known in the art.

Small holes may be located on the surface of the resected bone that were made by pins 70,72,74. Before prosthesis 120 is implanted, these holes may be filled with bone filler or any other biocompatible material that is known in the art for filing voids. Alternatively, the holes may not be filled and rather left open to fill in time naturally. The bone contacting surface may alternatively have pegs or projections protruding therefrom configured to be pressed into the small holes left by pins 70,72,74. Preferably, the bone contact surface of prosthesis 120 is flat and does not need such pegs or projections to remain engaged to the trochlear groove of the femur because the three overlapping recessed areas formed by cutting instruments 134,136,138 preferably conform and engage to the three overlapping areas 124,126,128 of prosthesis 120 that is implanted on the resected bone.

At least a portion of an outer surface 122 of the prosthesis preferably includes a curved recessed region 130 that approximates the natural anatomical structure of the trochlear groove of the patient's femur in a pre-degenerated state. Each prosthesis therefore has a trochlear groove with a curvature that closely approximates that of the affected knee.

The system of the present invention may include other features in use as well. First drill pin 70 is adapted to secure proximal section 20 of guide 10 to bone of the trochlear groove 8 of femur 2 along curve 9. Proximal section 20 and intermediate section 40 of guide 10 generally form an angle Q as shown in FIG. 3. Intermediate section 40 extends distally from proximal section 20 at angle Q such that intermediate section 40 and proximal section 20 lay adjacent trochlear groove 8 of femur 2.

First guide hole 26 of guide 10 preferably includes a first longitudinal axis 31 and second guide hole 46 includes a second longitudinal axis 33, wherein first longitudinal axis 31 is oriented at an angle with respect to second longitudinal axis 33. Third guide hole 48 includes a third longitudinal axis 35, wherein third longitudinal axis 35 is preferably parallel to second longitudinal axis 33. In an embodiment first, second and third guide holes may be parallel to one another. Alternatively, first, second and third guide holes may not be parallel to one another.

A method of preparing the trochlear groove of a patient's femur to receive a prosthesis thereon may include placing a guide 10 along the trochlear groove 8 of femur 2, the guide 10 having a proximal section 20 adapted to engage trochlear groove 8 along a curve 9 thereof. Proximal section 20 preferably has a first guide hole 26 therethrough. Guide 10 preferably includes an intermediate section 40 extending distally from proximal section 20, the intermediate section 40 having a second guide hole 46 therethrough and a third guide hole 48 therethrough. First guide hole 26 is preferably located laterally of second guide hole 46 and third guide hole 48. The method further includes inserting a first guide pin 70 through first guide hole 26 until first guide pin 70 is secured into bone of femur 2. A second guide pin 72 may be inserted through second guide hole 46 until second guide pin 72 is secured into bone of femur 2. A third guide pin 74 may be inserted through third guide hole 48 until third guide pin 74 is secured into bone of femur 2.

In order to remove guide 10 from its position on trochlear groove 8 of femur 2 such that guide 10 does not surround any of the first, second, or third guide pins 70,72,74, one or more of these pins may have to be removed and then replaced into bone of femur 2 after guide 10 is removed. The method may further include placing a first bone cutting instrument 134 having a guide hole therein against a first bone surface of the trochlear groove such that first guide pin 70 is located in the guide hole of the first bone cutting instrument. Bone cutting instrument 134 may then be rotated in order to form a first recess in the bone of the femur. The method may further include placing a second bone cutting instrument 136 having a guide hole therein against a second bone surface of the trochlear groove such that second guide pin 72 is located in the guide hole of the second bone cutting instrument. Bone cutting instrument 136 may then be rotated in order to form a second recess in the bone of the femur. The method may further include placing a third bone cutting instrument 138 having a guide hole therein against a third bone surface of the trochlear groove such that third guide pin 74 is located in the guide hole of the third bone cutting instrument.

According to this method, first bone cutting instrument 134 removes bone along a first plane perpendicular to a longitudinal axis 31 of the guide hole of first bone cutting instrument 134. Second bone cutting instrument 136 removes bone along a second plane perpendicular to a longitudinal axis 33 of the guide hole of second bone cutting instrument 136, the second plane preferably oriented at an angle with respect to the first plane. Third bone cutting instrument 138 removes bone along a third plane perpendicular to a longitudinal axis 35 of the guide hole of third bone cutting instrument 138, the third plane preferably parallel to the second plane.

In one embodiment, third bone cutting instrument 138 may remove bone along a third plane perpendicular to longitudinal axis 35 of the guide hole of third bone cutting instrument 138, wherein the third plane may not be parallel to the second plane. Alternatively, first, second, and third bone cutting instruments 134,136,138 may remove bone along first, second, and third longitudinal axes respectively, wherein the first, second, and third longitudinal axes of the bone cutting instruments are parallel to one another. Alternatively, the first, second, and third bone cutting instruments 134,136,138 may remove bone along first, second, and third longitudinal axis respectively, wherein the first, second, and third longitudinal axes of the bone cutting instruments may not be parallel to one another.

Preferably, first bone cutting instrument 134 has a first diameter, second bone cutting instrument 136 has a second diameter, and third bone cutting instrument 138 has a third diameter, wherein the first diameter is larger than the second diameter, and the second diameter is larger than the third diameter.

In a method of implanting prosthesis 120 on resected bone, prosthesis 120 has first, second, and third sections 124,126, 128 corresponding to first, second, and third recesses formed by first, second, and third bone cutting instruments 134,136, 138 respectively. According to a method of the present invention, first reference guide 49 may be centered on the trochlear groove of the patient's femur in the intercondylar region, wherein the first reference guide extending in a medial-lateral direction from intermediate section 40. Second reference guide 64 may also be centered along transepicondylar axis 73 of the patient's femur, wherein second reference guide 64 preferably extends in a medial-lateral direction from distal section 60 of guide 10.

Figure 6:
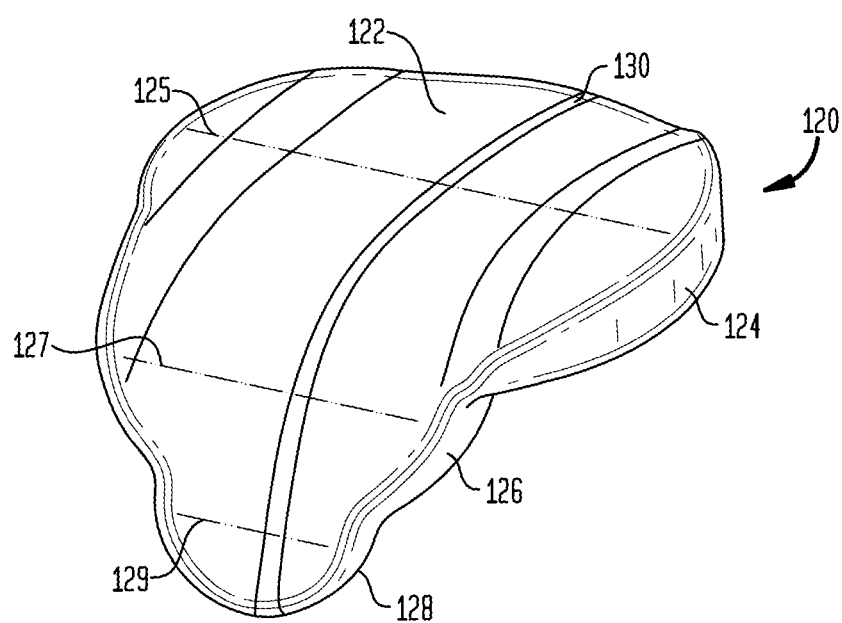
FIG. 6 is a perspective view of an embodiment of a prosthesis of the present invention.

FIGS. 6 and 7 show prosthesis 120 which is configured to be implanted in a prepared trochlear groove of a femur. Prosthesis 120 has a proximal section 124 having a first maximum height 142 in an anterior-posterior direction and a first diameter 125, an intermediate section 126 having a second maximum height 146 in an anterior-posterior direction and a second diameter 127, and a distal section 128 having a third maximum height 150 in an anterior-posterior direction and a third diameter 129. Preferably, the second maximum height 146 is less than the first maximum height 142, and the third maximum height 150 is less than the second maximum height 146. Preferably, the proximal, intermediate, and distal sections of prosthesis 120 each have a side surface between the outer surface and bone contacting surface thereof, the side surfaces forming the first, second, and third diameters 125, 127,129 of the proximal, intermediate, and distal sections 124,126,128 respectively.

As shown in FIG. 6, proximal section 124, intermediate section 126, and distal section 128 of prosthesis 120 each have an outer surface 122 with a continuous groove 130. Groove 130 is configured to engage an articular surface of a patella (not shown). Preferably, groove 130 of prosthesis 120 approximates the trochlear groove of the patient in a pre-degenerated state. By implanting prosthesis 120 on the resected bone, the trochlear groove of the patient may therefore be restored.

Figure 8:
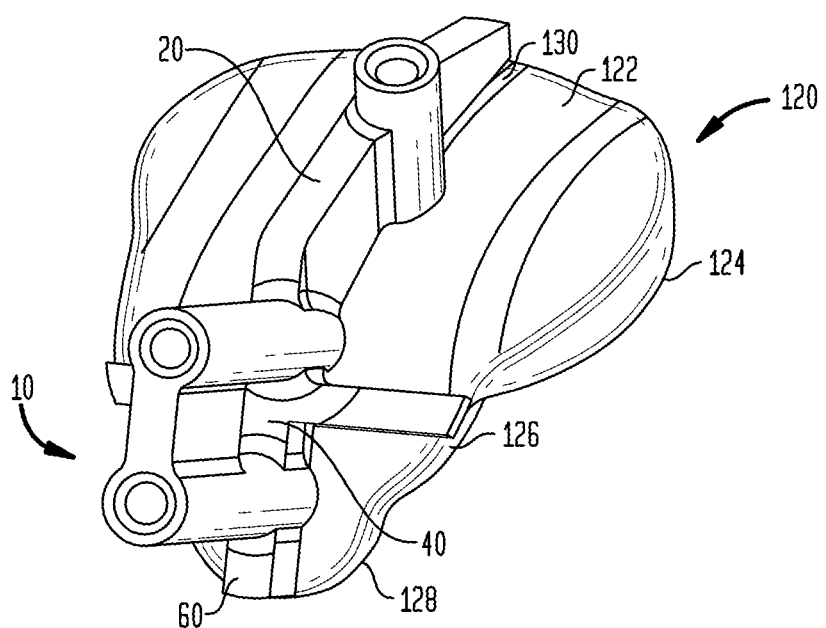
FIG. 8 is a perspective view of the guide of FIG. 1 positioned on the outer surface of the prosthesis of FIG. 6.

As shown in FIG. 8, the proximal, intermediate, and distal sections of guide 10 relate to the proximal, intermediate, and distal sections of prosthesis 120. Guide 10 is shown lying on top of outer surface 122 of prosthesis 120 in order to show the configuration of guide 10 and prosthesis 120 in relation to one another. It should be understood that at no time during a method of the present invention is guide 10 placed on top of prosthesis 120.

Figure 12:
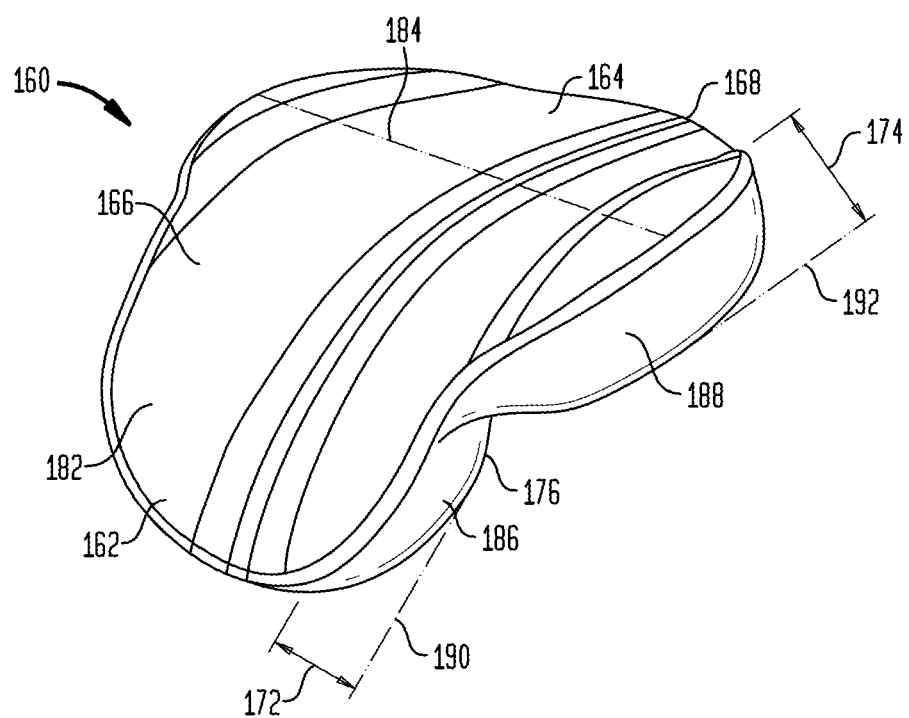
FIG. 12 is a perspective view of an alternative embodiment of a prosthesis of the present invention.

As shown in FIG. 12, a prosthesis 160 for implantation in a prepared trochlear groove of a femur of the present invention may alternatively have two sections rather than three sections as described with respect to prosthesis 120. Such a prosthesis preferably has a first section 162 having a first maximum height 172 in an anterior-posterior direction and a first diameter 182, and a second section 164 having a second maximum height 174 in an anterior-posterior direction and a second diameter 184, wherein the second maximum height 174 is less than the first maximum height 172.

Preferably, first and second sections 162,164 of prosthesis 160 each have an outer surface 166 with a continuous groove 168 configured to engage an articular surface of a patella (not shown). Preferably, first and second sections 162,164 each have a generally flat bone contacting surface 176. Preferably, first and second sections 162,164 each have a side surface 186,188 between outer surface 166 and bone contacting surface 176 thereof, side surfaces 186,188 forming first and second diameters 182,184 of first and second sections 162, 164 respectively. Preferably, flat bone contacting surface 176 of first section 162 lies along a plane 190 oriented at an angle with respect to a plane of the second section 192. Preferably, diameter 184 of prosthesis 160 according to this aspect is greater than diameter 182.

While the systems and methods that are described herein generally include the use of prostheses, guide and instruments corresponding thereto, and cutting instruments each utilized to replace a damaged trochlear groove region of a patient, such systems and methods may also be utilized for replacing a damaged condyle in a unicondylar knee replacement. A guide used in such a procedure aides in resecting a condyle such that a unicondylar prosthesis may be implanted on the resected bone. Such a system may include a family of multiple sized unicondylar prostheses, a combination drill-and-alignment guide corresponding to each prosthesis, a flexible sizing membrane corresponding to each prosthesis, a series of guide pins to insert in guide holes of the combination drill-and-alignment guide, and a series of bone cutting instruments or reamers corresponding to specific sections of each prosthesis.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A joint replacement system for replacing at least a portion of a trochlear groove of a femur comprising:
a guide having a contacting surface defined by a central body portion and lateral portions, the contacting surface including a proximal end, a distal end and lateral ends, the proximal and distal ends located at opposing ends of the central body portion and the lateral ends located at opposing ends of the lateral portions;
a prosthesis having an articular surface and a contacting surface, the articular surface including a perimeter having proximal, distal and lateral end portions; and
a sizing membrane configured to correctly position the guide on the trochlear groove of the femur, the sizing membrane having an outer surface, a contacting surface and a perimeter having a shape substantially the same as the perimeter of the articular surface of the prosthesis, wherein the proximal end, distal end and lateral ends of the contacting surface of the guide correspond to the proximal, distal and lateral end portions of the perimeter of the articular surface of the prosthesis.

2. The joint replacement system of claim 1, further comprising an outer surface opposed to the contacting surface of the central body portion, wherein at least one guide hole extends through the outer and contacting surfaces of the central body portion.

3. The joint replacement system of claim 1, wherein the central body portion is curved such that when the contacting surface of the central body portion contacts the trochlear groove of the femur in a desired position, the entire contacting surface of the central body portion lies along the trochlear groove.

4. The joint replacement system of claim 3, wherein when the contacting surface of the curved central body portion lies along the trochlear groove in the desired position, the proximal end thereof lies adjacent an anterior cortex of the femur and the distal end thereof lies adjacent an intercondylar notch of the femur.

5. The joint replacement system of claim 1, wherein the central body portion includes a first section having a first longitudinal axis and a second section having a second longitudinal axis, the first and second longitudinal axes being angled with respect to each other.

6. The joint replacement system of claim 1, wherein the contacting surface of the guide is configured to have at least four points of contact with the femur when the guide contacts the femur in a desired position, the four points of contact formed by the proximal end, distal end and lateral ends of the contacting surface of the guide.

7. The joint replacement system of claim 1, wherein the sizing membrane is flexible such that the contacting surface thereof conforms to a shape of a surface it is brought in contact with.

8. The joint replacement system of claim 1, wherein the perimeter of the sizing membrane defines proximal, distal and lateral end portions of the contacting surface of the sizing membrane, and wherein the proximal end, distal end and lateral ends of the contacting surface of the guide correspond to the proximal, distal and lateral end portions of the perimeter of the contacting surface of the sizing membrane.

9. The joint replacement system of claim 1, wherein the lateral portions extend outwardly in opposing directions from the central body portion of the guide.

10. A method of replacing a joint comprising:
contacting the joint with a contacting surface of a sizing membrane configured to correctly position a guide on a trochlear groove of a femur, the sizing membrane having an outer surface, a contacting surface and a perimeter having a shape substantially the same as a perimeter of an articular surface of a prosthesis;
orienting a contacting surface of a guide on the outer surface of the membrane such that a proximal end, a distal end and lateral ends of the contacting surface of the guide are adjacent proximal, distal and lateral end portions of the perimeter of the sizing membrane;
resecting at least a portion of the joint with the guide; and
implanting the prosthesis on the at least a portion of the resected joint.

11. The method of claim 10, further comprising:
orienting the sizing membrane with respect the joint in a desired location for implanting the prosthesis.

12. The method of claim 10, further comprising:
creating at least one reference marking in a surface of the joint with the guide.

13. The method of claim 12, further comprising:
piercing the sizing membrane with a guide pin in creating the at least one reference marking.

14. The method of claim 13, further comprising:
using the guide pin to guide the resecting of the at least a portion of the joint.

15. The method of claim 10, wherein the perimeter of the membrane has a shape substantially the same as a perimeter of the articular surface of the prosthesis.

16. The joint replacement system of claim 15, wherein the sizing membrane is flexible such that the contacting surface thereof conforms to a shape of a surface it is brought in contact with.

17. The method of claim 10, wherein the prosthesis has a contacting surface, the articular surface including a perimeter having proximal, distal and lateral end portions corresponding to the proximal, distal and lateral end portions of the perimeter of the sizing membrane.

18. The joint replacement system of claim 10, wherein the guide includes first and second lateral portions.

19. The joint replacement system of claim 18, wherein the first and second lateral portions each extend outwardly in opposing directions from an elongate central body.

20. The joint replacement system of claim 19, wherein the elongate central body terminates at the proximal and distal ends of the contacting surface of the guide.

\* \* \* \* \*